United States Patent
Kim et al.

(10) Patent No.: US 9,420,963 B2
(45) Date of Patent: Aug. 23, 2016

(54) APPARATUS AND METHOD FOR RECOGNIZING USER'S POSTURE IN HORSE-RIDING SIMULATOR

(71) Applicant: Electronics and Telecommunications Research Institute, Daejeon (KR)

(72) Inventors: Kye Kyung Kim, Daejeon (KR); Sang Seung Kang, Daejeon (KR); Suyoung Chi, Daejeon (KR); Dong-Jin Lee, Daejeon (KR); Yun Koo Chung, Daejeon (KR); Mun Sung Han, Daejeon (KR); Jae Hong Kim, Daejeon (KR); Jong-Hyun Park, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 219 days.

(21) Appl. No.: 14/244,301

(22) Filed: Apr. 3, 2014

(65) Prior Publication Data
US 2015/0051512 A1    Feb. 19, 2015

(30) Foreign Application Priority Data
Aug. 16, 2013    (KR) .......................... 10-2013-0097481

(51) Int. Cl.
*A61B 5/00*    (2006.01)
*A61B 5/11*    (2006.01)

(52) U.S. Cl.
CPC ............. *A61B 5/1128* (2013.01); *A61B 5/1121* (2013.01); *A61B 2503/10* (2013.01)

(58) Field of Classification Search
CPC ........ A61B 5/11; A61B 5/1116; A61B 5/112; A61B 5/1121; A61B 5/1128; A61B 2503/10; G09B 19/0038; A63K 3/00
See application file for complete search history.

(56) References Cited

U.S. PATENT DOCUMENTS

| | | | | |
|---|---|---|---|---|
| 4,935,887 A | * | 6/1990 | Abdalah et al. | 703/6 |
| 4,988,300 A | * | 1/1991 | Yamaguchi et al. | 434/247 |
| 6,599,198 B2 | * | 7/2003 | Ettenhofer | 472/104 |

(Continued)

FOREIGN PATENT DOCUMENTS

| | | |
|---|---|---|
| JP | 2010-178777 | 8/2010 |
| KR | 10-2011-0133959 | 12/2011 |
| KR | 10-2012-0105315 | 9/2012 |

OTHER PUBLICATIONS

Kyekyung Kim et al., "Object Recognition on Horse Riding Simulator System", WASET 2013: World Academy of Science, Engineering and Technology, May 22-23, 2013, pp. 655-659.

(Continued)

*Primary Examiner* — Max Hindenburg
(74) *Attorney, Agent, or Firm* — Kile Park Reed & Houtteman PLLC

(57) ABSTRACT

An apparatus for recognizing a user's posture in a horse-riding simulator, the apparatus comprising: a standard posture model generation module configured to find out a standard posture model by selecting feature points from an expert database, and generate the standard posture model; and a posture recognizing module configured to obtain a user's posture from the horse-riding simulator, recognize a user's horse-riding posture by matching the obtained user's posture with the standard posture model generated in the standard posture model generation module, and suggest a standard posture model appropriate for a user's level.

16 Claims, 11 Drawing Sheets

SIDE POSTURE FEATURE POINT

(56) References Cited

U.S. PATENT DOCUMENTS 7,749,088 B2 * 7/2010 Greenwood .................... 472/97
9,159,245 B2 * 10/2015 Smith et al.

OTHER PUBLICATIONS

Kye-kyung Kim et al., "User Identification and Pose Recognition on Horse Riding Simulator", Electronics and Telecommunications Research Institute, vol. 1, No. 1, Jul. 11-13, 2013.

* cited by examiner

SIDE POSTURE IMAGE

SIDE POSTURE IMAGE

REAR POSTURE IMAGE

REAR POSTURE IMAGE

SIDE POSTURE FEATURE POINT

REAR POSTURE FEATURE POINT

SIDE POSTURE FEATURE POINT

REAR POSTURE FEATURE POINT

SIDE POSTURE NORMALIZATION

REAR POSTURE NORMALIZATION

⊙ POSTURE REFERENCE POINT

● POSTURE FEATURE POINT

— POSTURE FEATURE POINT CHANGE LINE

DISTANCE BETWEEN SIDE
POSTURE FEATURE POINTS

DISTANCE BETWEEN REAR
POSTURE FEATURE POINTS

⟵⟶ VERITCAL DIATANCE BETWEEN
POSTURE FEATURE POINTS

BASIC LEVEL SIDE POSTURE FEATURE POINTS

ADVANCED LEVEL SIDE POSTURE FEATURE POINTS

PERSONALIZED SIDE POSTURE AREA

PERSONALIZED REAR POSTURE AREA

BASIC LEVEL AREA

MIDDLE LEVEL AREA

HIGH LEVEL AREA

APPARATUS AND METHOD FOR RECOGNIZING USER'S POSTURE IN HORSE-RIDING SIMULATOR

RELATED APPLICATIONS

This application claims the benefit of Korean Patent Application No. 10-2013-0097481, filed on Aug. 16, 2013, which is hereby incorporated by reference as if fully set forth herein.

FIELD OF THE INVENTION

The present invention relates to a system for recognizing a user's posture in a horse-riding simulator. More particularly, the present invention relates to an apparatus and method for recognizing a user's posture in a horse-riding simulator, capable of generating a standard posture model using collected horse-riding posture images of experts, matching posture characteristics extracted from a user's horse-riding image with the standard posture model, determining a user's horse-riding level with a user's posture recognized through the matching, and suggesting a progressive standard posture model suitable to an individually differentiated lesson, thereby providing a lesson in consideration of an individual horse-riding level.

BACKGROUND OF THE INVENTION

Recently, an interest in private health has become a large issue to ordinary people as well as older people and disabled people. Running machines developed by US department of defense in 1950' for physical test of soldiers are increasingly demanded since then in fitness centers to manage physical strength for ordinary people. Currently, the private health management is more than a simple concept of sport equipments and is integrated into an advanced IT technology, a robot technology and a bio-signal measurement and analysis technology, achieving an innovative development in automatic and personalized healthcare management types. Among them, the trend is that an image information process technology in which private health is monitored and cared using visual sensor information is integrated into other technologies such as robot technology, developing into a new IT fusion solution technology.

With the development of such technologies, a process of obtaining and monitoring an exercise procedure of an exerciser using a sensor, analyzing relevant information and feeding back exercise results and effects again is being executed in medical equipment, rehabilitation equipment, aging-friendly equipment and exercise equipment.

Especially, since image information using a visual sensor provides functions to obtain and analyze posture information of an exerciser, and correct the posture, it is true that the information is widely used to increase a private exercise ability or physical strength. Further, an IT technology to find out and recognize a specific object area out of an image that has obtained an exercise procedure of an exerciser has been used in golf and skate so as to provide a user's posture correction and personalized coaching.

For example, in case of golf, a study has been progressed to obtain exercise posture information of a user using a visual sensor, and analyze and correct a swing posture, or obtain exercise motion in a precise level with a sensor attached to a body, and analyze and correct posture information.

Meanwhile, with a highly-elated interest in horse-riding recently and a sharp increase of horse-riding people, a study is being progressed to train a horse-riding posture and provide a personalized service using a horse-riding simulator indoor. However, it is true that a study for recognizing and coaching a user's horse-riding posture using a visual sensor is imperceptible until now and there is an increased demand of a horse-riding posture recognition technology using a vision sensor in order to be used in a posture recognition training of general users.

SUMMARY OF THE INVENTION

In view of the above, the present invention provides an apparatus and method for recognizing a user's posture in a horse-riding simulator, capable of generating a standard posture model using collected horse-riding posture images of experts, matching posture characteristics extracted from a user's horse-riding image with the standard posture model, determining a user's horse-riding level with a user's posture recognized through the matching, and suggesting a progressive standard posture model suitable to an individually differentiated lesson, thereby providing a lesson in consideration of an individual horse-riding level.

With the apparatus and method for recognizing a user's posture in a horse-riding simulator of the present invention, there is an advantage of providing a lesson in consideration of an individual horse-riding level by generating a standard posture model using collected horse-riding posture images of experts from a horse-riding simulator, matching posture characteristics extracted from a user's horse-riding image with the standard posture model, determining a user's horse-riding level with a user's posture recognized through the matching, and suggesting a progressive standard posture model suitable to an individually differentiated lesson.

In accordance with a first embodiment of the present invention, there is provided an apparatus for recognizing a user's posture in a horse-riding simulator, the apparatus comprising: a standard posture model generation module configured to find out a standard posture model by selecting feature points from an expert database, and generate the standard posture model; and a posture recognizing module configured to obtain a user's posture from the horse-riding simulator, recognize a user's horse-riding posture by matching the obtained user's posture with the standard posture model generated in the standard posture model generation module, and suggest a standard posture model appropriate for a user's level.

In the embodiment, the standard posture model generation module comprises: a posture image input unit configured to input horse-riding posture images of an expert; a feature point selecting unit configured to extract positions of a body from the horse-riding posture images of an expert inputted from the posture image input unit and select feature points in the posture image; a posture image normalizing unit configured to normalize the horse-riding posture images of an expert inputted from the posture image collecting input unit; an average position and deviation extracting unit configured to calculate an average position of the posture feature points inputted from the feature point selection unit and extract a deviation of the posture image from the average position; a posture deviation pattern analyzing unit configured to analyze a posture deviation and change pattern from various posture images produced depending on a user's level or walking pattern of a horse; and a posture model generation unit configured to generate the standard posture model by applying the posture deviation and change pattern analyzed in the posture deviation pattern analyzing unit.

In the embodiment, the posture image collection inputting unit is configured to input the posture images of an expert from the expert database that stores the horse-riding posture images of an expert.

In the embodiment, the feature point selecting unit extracts positions of shoulder, elbow, hands or feet from the horse-riding images and selects characteristics of the posture image.

In the embodiment, the posture recognizing module comprises: an image acquisition unit configured to acquire a user's posture image; a posture detecting unit configured to separate the posture area from the user's posture image obtained from the image acquisition unit and detect a user's posture; a user's posture characteristic extracting unit configured to extract a body position of a user from the posture area and detect a posture characteristic of the user; a characteristic normalizing unit configured to normalize the posture characteristic of the user detected from the user's posture characteristic detecting unit; and a recognizing unit configured to recognize the user's horse-riding posture by matching the user's horse-riding posture with a standard posture model.

In the embodiment, the posture detecting unit is configured to detect the user's posture by minimizing a surrounding environment effect for the user's posture image obtained from the image acquisition unit and correctly separating only the posture area of the user.

In the embodiment, the user's posture characteristic extracting unit is configured to detect the posture characteristic of the user by extracting positions of shoulder, elbow, hands or feet from the posture area of the user.

In the embodiment, the recognizing unit is configured to recognize the user's horse-riding posture by matching the user's posture with the standard posture model generated in the standard posture model generating unit and suggest a standard posture model appropriate for a user's level.

In the embodiment, the image acquisition unit is configured to obtain the user's posture image through a vision sensor.

In accordance with a first embodiment of the present invention, there is provided a method for recognizing a user's posture in a horse-riding simulator, the method comprising: finding out a standard posture model by selecting posture feature points from an expert database to generate the standard posture model; and obtaining a user's posture from the horse-riding simulator to recognize a user's horse-riding posture by matching the obtained user's posture with the standard posture model.

In the embodiment, said generating the standard posture model comprises: inputting horse-riding posture images of an expert; extracting positions of a body from the horse-riding posture images of an expert to select posture feature points in the posture image; normalizing the horse-riding posture images of an expert; calculating an average position of the posture feature points and extracting a deviation of the posture image from the average position; analyzing a posture deviation and change pattern from various posture images produced depending on a user's level or walking pattern of a horse; and generating a standard posture model by applying the analyzed posture deviation and change pattern.

In the embodiment, the horse-riding posture image is inputted from an expert database that stores the horse-riding posture images of an expert.

In the embodiment, the posture feature point is selected by extracting positions of shoulder, elbow, hands or feet from the horse-riding image.

In the embodiment, said recognizing the user's horse-riding posture comprises: acquiring a user's posture image; separating a user's posture area from the user's posture image obtained and detecting a user's posture; detecting a posture characteristic of the user by extracting a body position of the user from the posture area of the user; normalizing the detected posture characteristic of the user; and recognizing a user's horse-riding posture by matching a user's horse-riding posture with a standard posture model.

In the embodiment, said detecting the posture characteristic of the user comprises extracting positions of shoulder, elbow, hands or feet from the user's posture area to detect the posture characteristic.

In the embodiment, the method further comprising: recognizing a user's horse-riding posture; and suggesting a standard posture model appropriate for a user's level.

BRIEF DESCRIPTION OF THE DRAWINGS

The above and other objects and features of the present invention will become apparent from the following description of embodiments given in conjunction with the accompanying drawings, in which.

DETAILED DESCRIPTION OF THE EMBODIMENTS

Hereinafter, embodiments of the present invention will be described in detail with reference to the accompanying drawings. In the following description, well-known functions or constitutions will not be described in detail if they would unnecessarily obscure the embodiments of the invention. Further, the terminologies to be described below are defined in consideration of functions in the invention and may vary depending on a user's or operator's intention or practice.

Accordingly, the definition may be made on a basis of the content throughout the specification.

Figure 1:
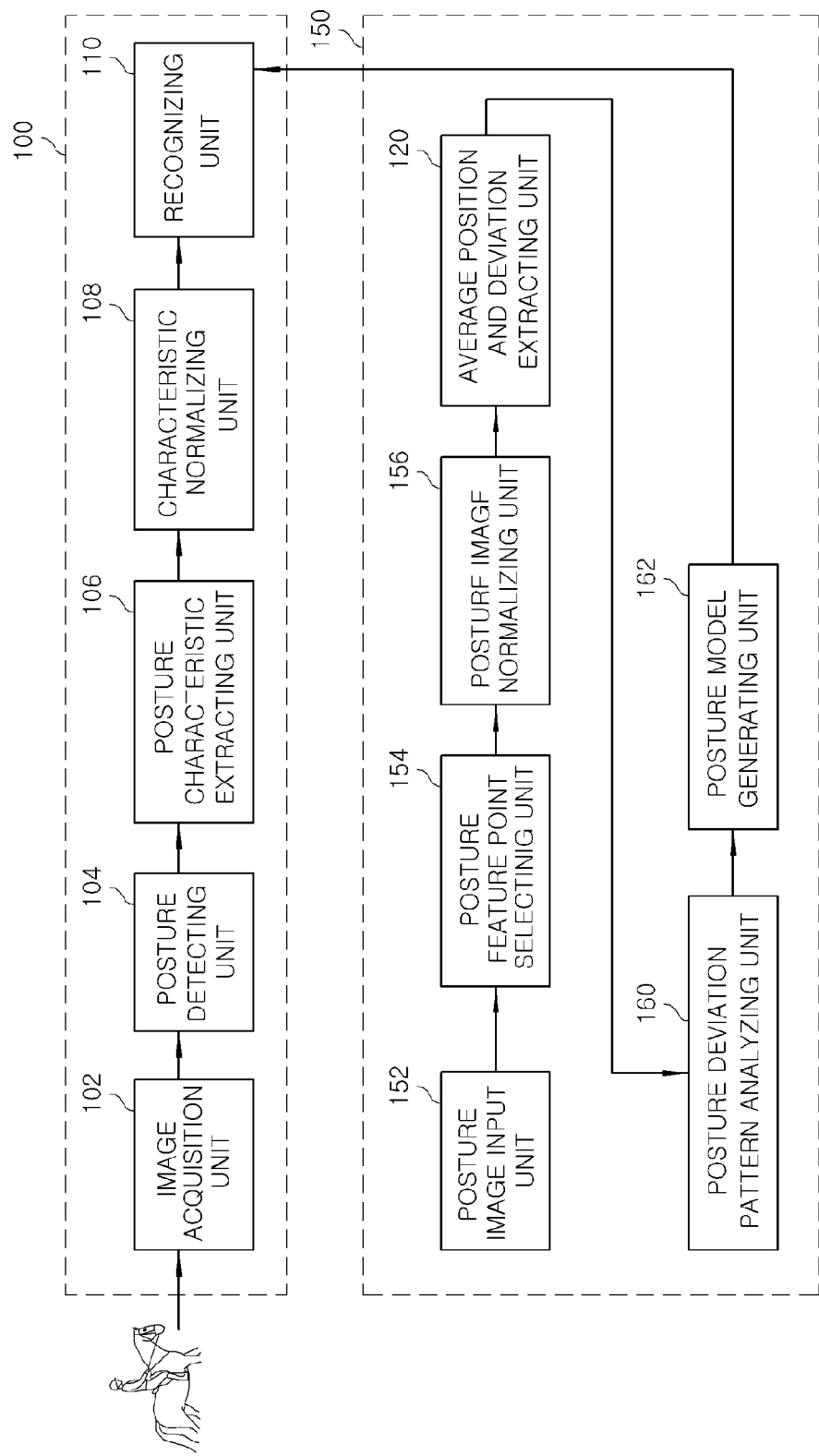
FIG. 1 is a detailed block diagram of an apparatus for recognizing a user's posture in a horse-riding simulator in accordance with an embodiment of the present invention.

FIG. 1 is a detailed block diagram of an apparatus for recognizing a user's posture in a horse-riding simulator in accordance with an embodiment of the present invention.

Referring to FIG. 1, the apparatus of recognizing a user's posture generally includes a posture recognizing module 100 and a standard posture model generating module 150.

First, the standard posture model generating module 150 finds out a standard posture model by selecting posture feature points from an expert's database and generates the standard posture model.

Such a standard posture model generating module 150 includes a posture image input unit 152, a feature point selecting unit 154, a posture image normalizing unit 156, an average position and deviation extracting unit 158, a posture deviation pattern analyzing unit 160, and a posture model generating unit 162.

The posture image input unit 152 inputs posture images of the expert from the expert database that stores horse-riding posture images of the expert.

The feature point selecting unit 154 extracts positions of shoulder, elbow, hands and feet from the horse-riding posture images of the expert that are inputted from the posture image input unit 152 and selects feature points in the posture images.

The posture image normalizing unit 156 normalizes the horse-riding posture images of the expert inputted from the posture image input unit 152.

The average position and deviation extracting unit 158 calculates an average position of the posture feature points inputted from the feature point selecting unit 154 and extracts a deviation of the posture images using the average position.

The posture deviation pattern analyzing unit 160 analyzes posture deviation and change pattern from a variety of posture images produced for a user's level or walking pattern of a horse.

The posture model generating unit 162 generates a standard posture model by reflecting the posture deviation and change pattern generated from the posture deviation pattern analyzing unit 160.

Next, the user posture recognizing module 100 obtains a user's posture using a vision sensor in the horse-riding simulator, recognizes a user's horse-riding posture by matching the user's posture with the standard posture model generated in the standard posture model generating module 150, and suggests a standard posture model appropriate for the user's level.

Such a posture recognizing module 100 includes an image acquisition unit 102, a posture detection unit 104, a posture characteristic extracting unit 106, a characteristic normalizing unit 108, and a recognizing unit 110.

The image acquisition unit 102 acquires a user posture image through a vision sensor. The posture detecting unit 104 detects a user's posture by minimizing surrounding effects for the user posture image acquired from the image acquisition unit 102 and correctly separating only the posture area of the user. The posture characteristic extracting unit 106 extracts shoulder, elbow, hands and feet of a user from the posture area of the user and then detects a posture characteristic of the user.

The characteristic normalizing unit 108 normalizes the user posture characteristics detected from the posture characteristic detecting unit 106.

The recognizing unit 110 recognizes a user's horse-riding posture by matching a user's horse-riding posture and a standard posture model. That is, the recognizing unit 110 recognizes the user's horse-riding posture by matching the user's posture with the standard posture model generated in the standard posture model generating module 150 and suggests a standard posture model appropriate for the user's level.

Figure 2:
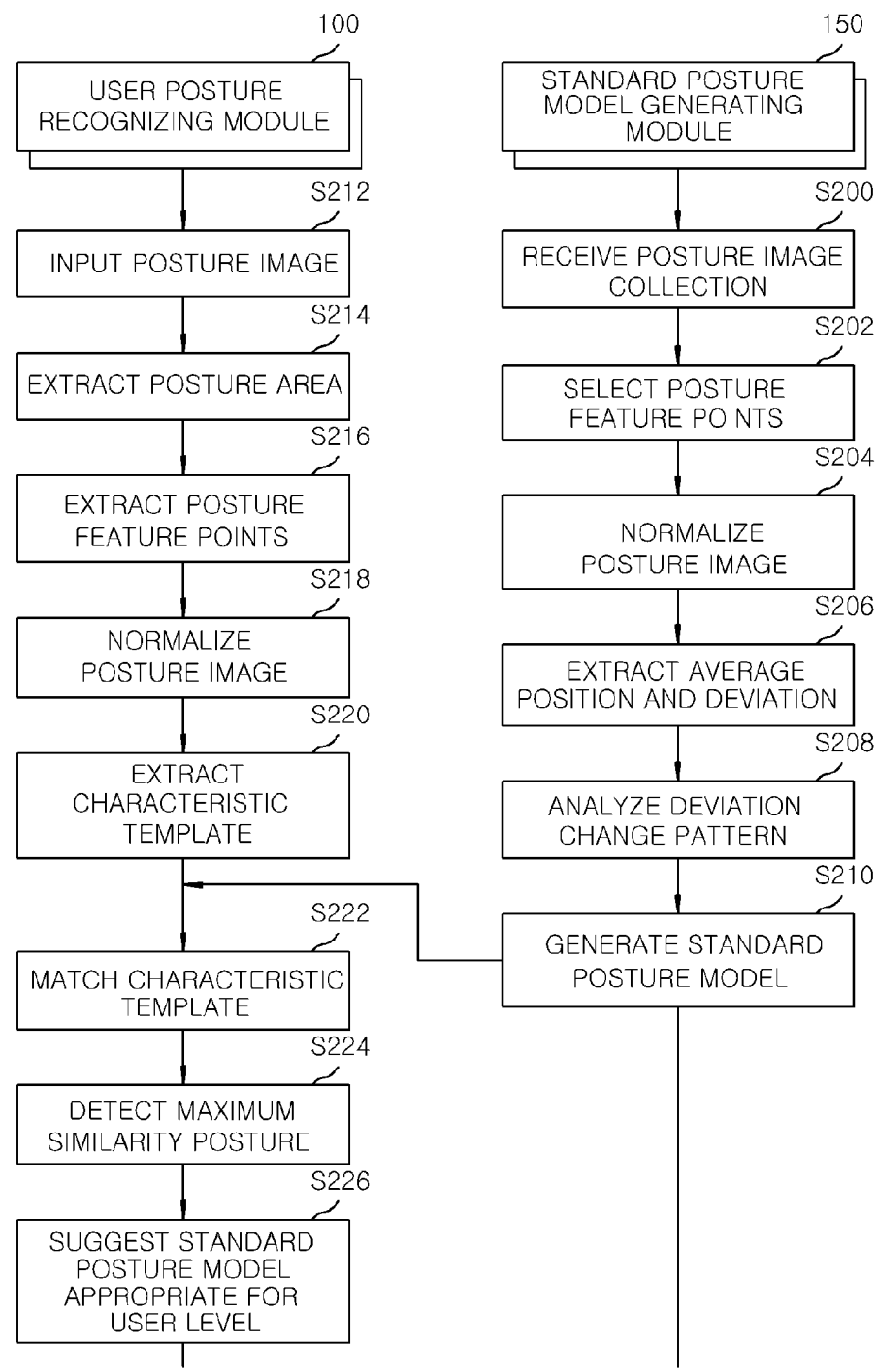
FIG. 2 is a sequential diagram illustrating a process for recognizing a user's posture in a horse-riding simulator in accordance with an embodiment of the present invention.

FIG. 2 is a sequential diagram of a process of recognizing a user's posture in a horse-riding simulator in accordance with an embodiment of the present invention. Hereinafter, an embodiment of the present invention will be described in detail with reference to FIGS. 1 and 2.

First, following is an operation of the standard posture model generating module 150. The standard posture model generating module 150 collects horse-riding posture images from a standard posture image database in order to recognize a user's horse-riding posture in block S200.

Next, the standard posture model generating module 150 selects posture feature points that are constituents of the standard posture model from the horse-riding images in block S202). In this case, the standard posture model generating module 150 may select the standard horse-riding posture images and then select the posture feature points from the selected horse-riding posture images.

Figure 3A:
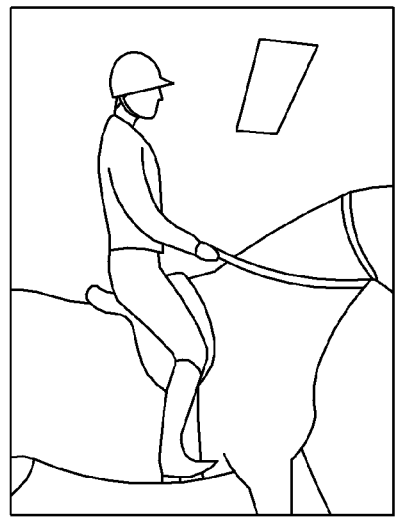
FIGS. 3A to 3D are illustrative posture images in a horse-riding simulator in accordance with an embodiment of the present invention.
Figure 3B:
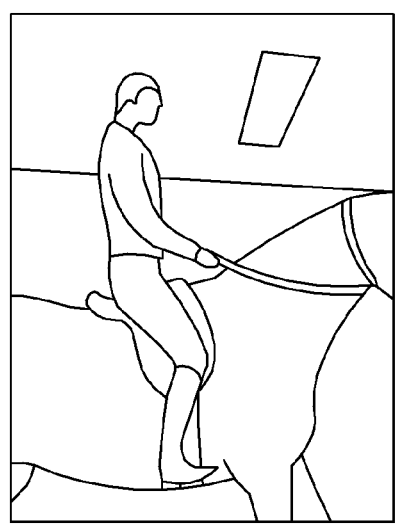
Figure 3C:
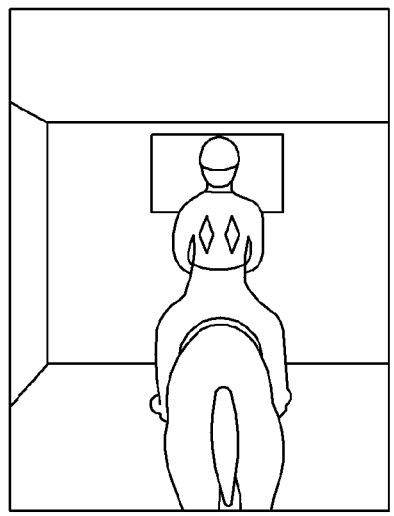
Figure 3D:
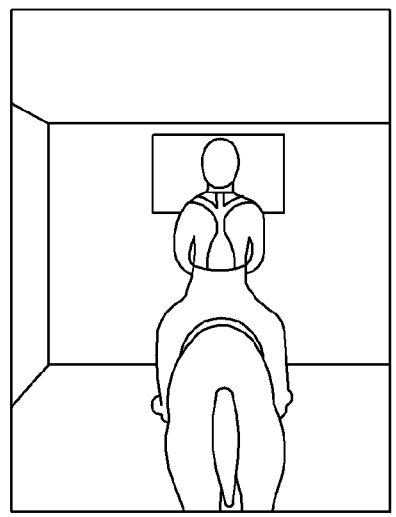

In addition, the standard horse-riding posture image may be constructed by selecting images that may be representative of the horse-riding posture from a variety of experts as shown in FIGS. 3A to 3D and then posture model images depending on a waling pattern of a horse. FIGS. 3A and 3B illustrate side posture images and FIGS. 3C and 3D illustrate rear posture images.

That is, referring to the horse-riding posture image illustrated in FIGS. 3A to 3D, the posture feature points constituting a plaster model may be waist unbending, position of hands holding reins and position of feet selected from posture images that are obtained from a side or rear view.

Figure 4A:
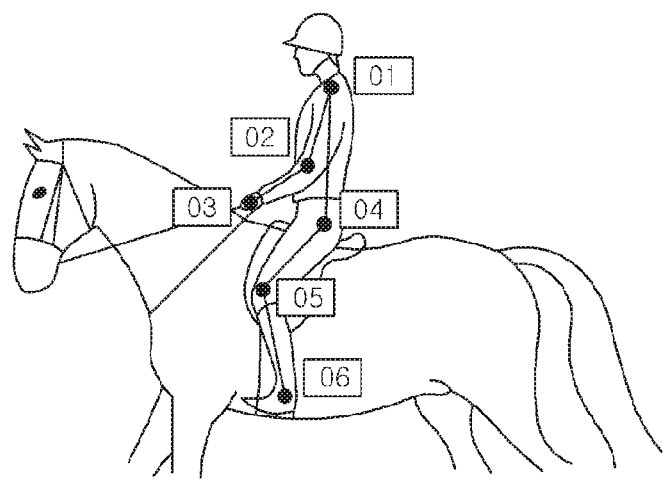
FIGS. 4A and 4B are illustrative views of showing posture feature points in a horse-riding simulator in accordance with an embodiment of the present invention.
Figure 4B:
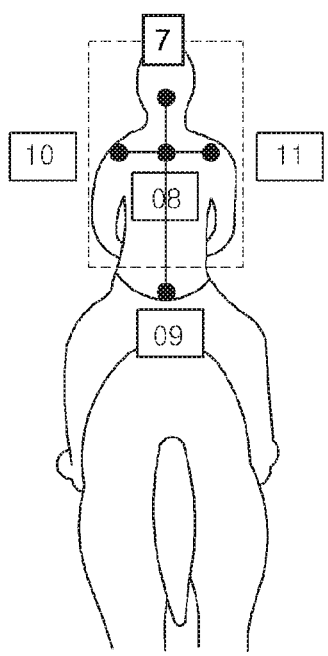

FIGS. 4A and 4B illustrate an example to select posture feature points in a horse-riding posture. When selecting side posture feature points, as illustrated in FIG. 4A, totally 6 feature points may be selected including feature points 01 and 04 corresponding to positions of shoulder and buttock to recognize waist unbending, feature points 02 and 03 corresponding to positions of elbow and hands to recognize the position of arms, and feature points 05 and 06 corresponding to knee and feet to recognize legs.

Further, when selecting rear posture feature points, as illustrated in FIG. 4B, four feature points may be selected, that is, 07, 09, 10 and 11 corresponding to positions of head, buttock, both shoulders from the rear posture image, and a feature point 08 may be selected as a basic feature point to recognize positions of shoulder, buttock, and head by extracting the maximum axis from a upper body area of the user and obtaining the center point of the upper body area. As such, a standard posture model may be generated by selecting total eleven feature points as feature points to recognize side and rear postures as illustrated in FIGS. 4A and 4B.

Figure 5A:
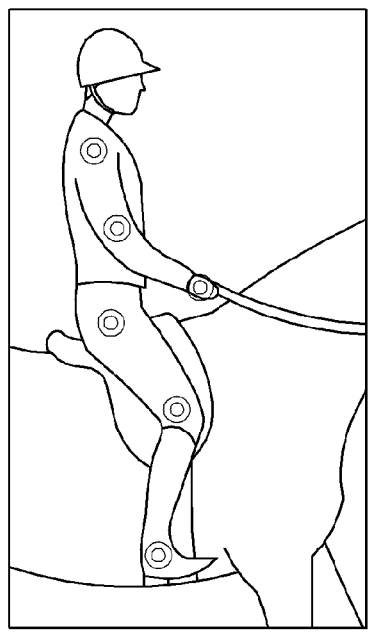
FIGS. 5A and 5B are illustrative images showing the extraction of posture feature points in a horse-riding simulator in accordance with an embodiment of the present invention.
Figure 5B:
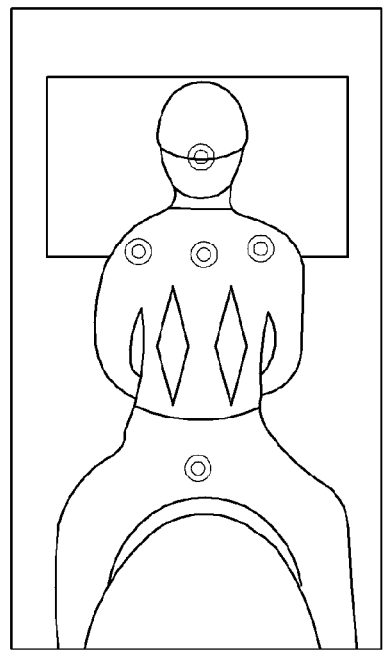

As illustrated in FIGS. 4A and 4B, the eleven posture feature points may be constituted of posture feature points 01 to 03, related with an upper posture such as shoulder, elbow and hands, side posture feature points 04 to 06 related with a lower posture such as buttocks, knee and feet, and rear posture feature points 07 to 11 related with head, shoulder and buttock. Further, such posture feature points may be constituted of points apart at a predetermined distance from an outline of a user's body, as illustrated in FIGS. 5A and 5B.

Figure 6A:
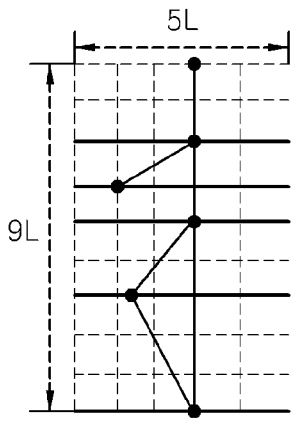
FIGS. 6A and 6B are illustrative views showing a user's posture characteristic normalization in a horse-riding simulator in accordance with an embodiment of the present invention.
Figure 6B:
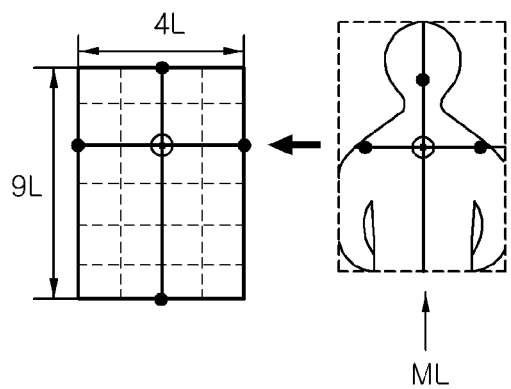
Figure 7A:
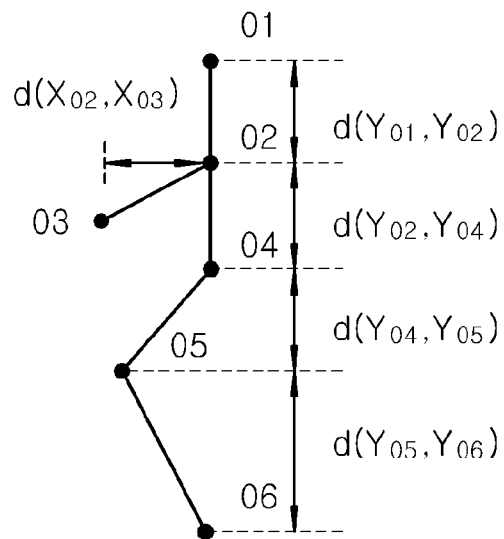
FIGS. 7A and 7B are illustrative views showing a distance calculation between posture feature points in a horse-riding simulator in accordance with an embodiment of the present invention.

Subsequently, the standard posture model generating module 150 normalizes the coordinates of the side and rear posture feature points on the basis of vertical distances and angles among the posture feature points, as illustrated in FIGS. 6A and 6B, in block S204. Such normalization of various posture images is a procedure that is necessarily needed to draw more correct posture recognition result while keeping the posture model consistent. First, the positions of the posture feature points are normalized. Next, the feature points in the posture image may be normalized in order that the distances among the feature points in the posture image in the vertical and horizontal directions are kept consistent as illustrated in FIGS. 7A and 7B.

In the normalization with respect to advanced side posture characteristic points, an angle between the feature points 01 and 02 is selected to be 90 degree and an angle between the feature points 02 and 03 is selected to be 210 degree when performed on the feature point 01 as a reference point and calculated with the feature point 02 as a center point; and an angle between the feature points 04 and 05 is selected to be 50 degree and an angle between the feature points 05 and 06 is selected to be 300 degree when calculated with the feature point 05 as a center point. At this time, the feature points 01, 02, 04 and 06 may exist on a straight line.

Figure 8A:
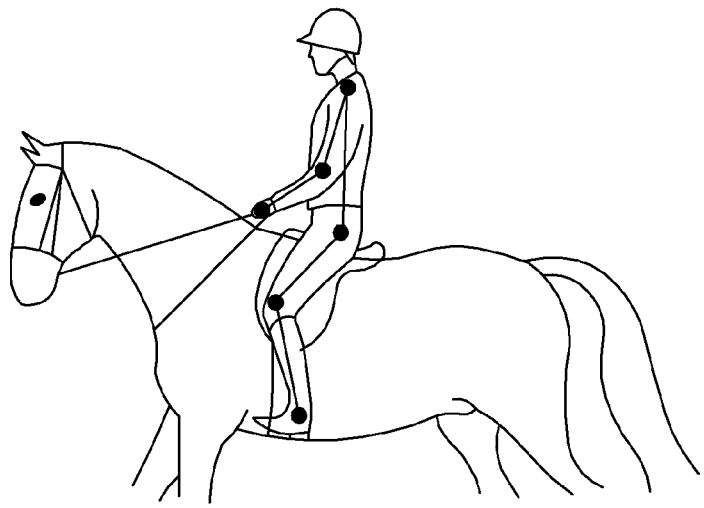
FIGS. 8A and 8B are illustrative views showing user's level based side posture feature points in a horse-riding simulator in accordance with an embodiment of the present invention.
Figure 8B:
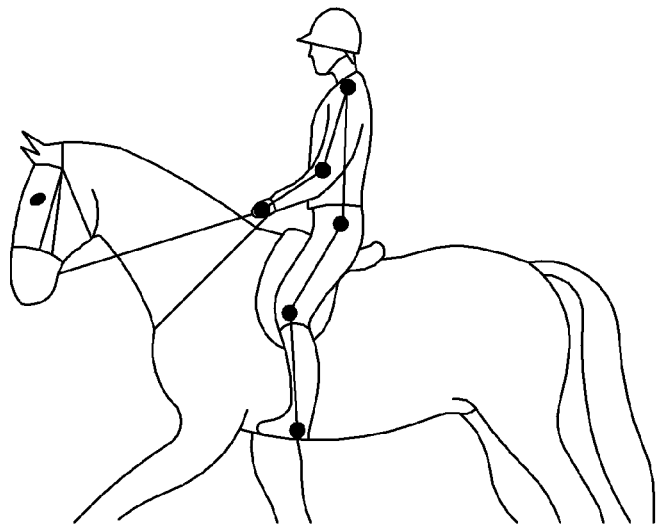

In the normalization with respect to basic level side posture feature points, an angle between the feature points 01 and 02 is selected to be 70 degree and an angle between the feature points 02 and 3 is selected to be 200 degree when calculated with the feature point 02 as a center point; and an angle between the feature points 04 and 05 is selected to be 40 degree and an angle between the feature points 05 and 06 is selected to be 285 degree when calculated with the feature point 05 as a center point. Further, it may be possible that an x-coordinate value of the feature point 06 exists on a position whose coordinate value is less than an x-coordinate value of the feature point 02 and greater than the feature point 05. The distance between neighboring feature points, that is, distances between the feature points 01 and 02, feature points 02 and 03, feature points 02 and 04, feature points 04 and 05, and feature points 05 and 06 may be determined constantly. FIGS. 8A and 8B illustrate feature points of a level based side posture.

Figure 7B:
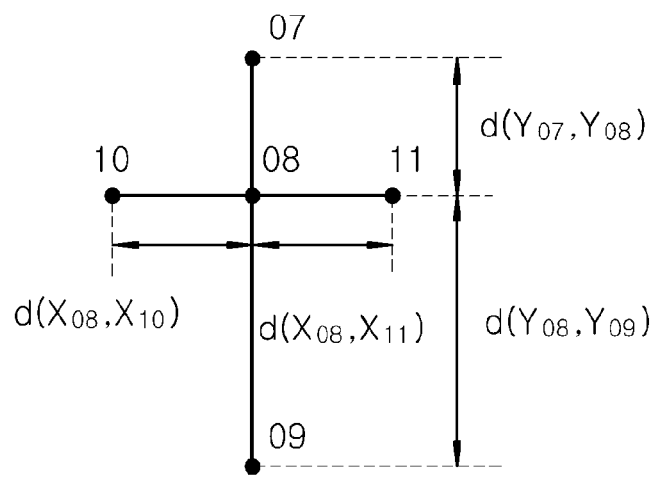

The rear posture feature points may be constituted in such a manner that, as illustrated in FIG. 7B, feature points and 09 are positioned on a straight line in the vertical direction, feature points 10 and 11 are positioned on a straight line in the horizontal direction, and coordinates of a straight line connecting the feature points 07 and 09 passes through a center point 08 of the feature points 10 and 11. The normalization may be performed such that the straight distance between the feature points 09 and 10 in the vertical direction is as twice as the straight distance between the feature points 07 and 10 in the horizontal direction.

Figure 9:
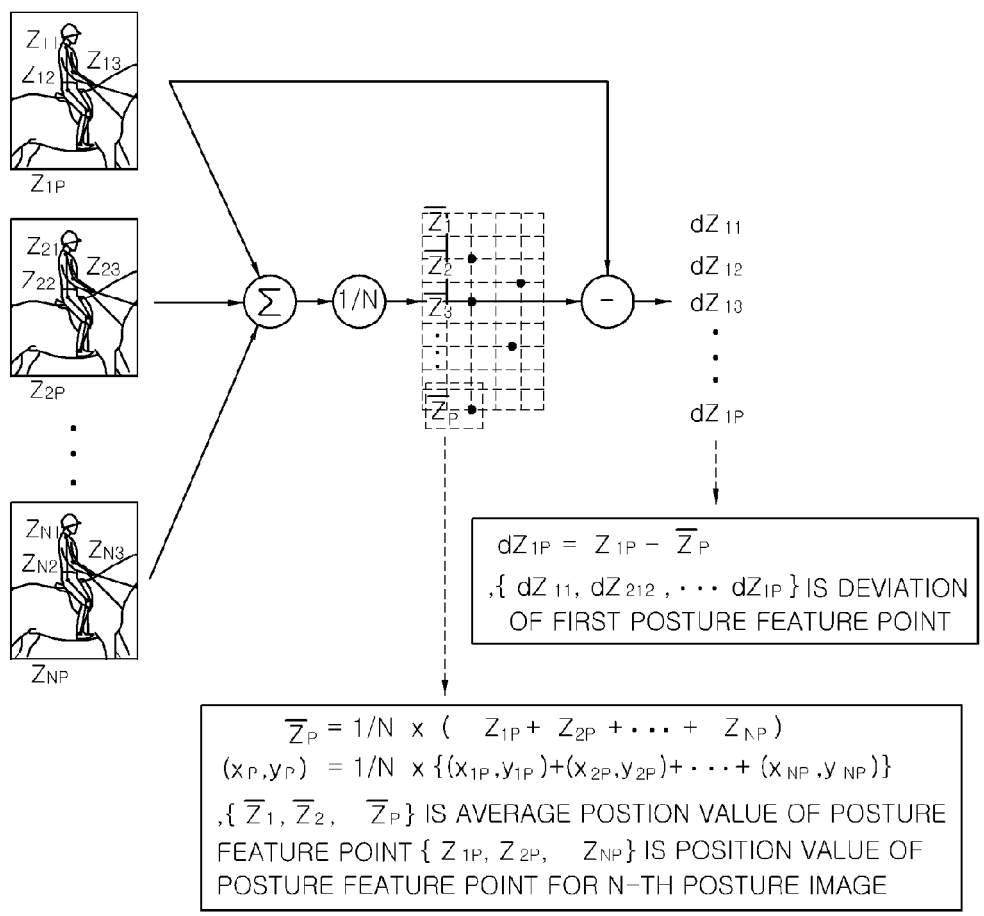
FIG. 9 is an illustrative view showing an average position and deviation of posture feature points in a horse-riding simulator in accordance with an embodiment of the present invention.

Next, the standard posture model generating module 150 obtains average position and deviation from each of the feature points in the standard posture images as illustrated in FIG. 9 in block S206. At this time, when obtaining the average position and deviation, the standard posture model generating module 150 may obtain position values of the posture feature points with respect to each standard posture image and then obtain a deviation from average position information.

The standard posture model typically indicates a posture model called a correct posture. Generally, considering walking patterns of a horse, a standard posture model of the correct posture may have a deviation within a predetermined range for each feature point. In consideration of such deviation, as illustrated in FIG. 9, a standard posture model may be generated by constructing a horse-riding posture image collection of a variety of experts, obtaining an average coordinate value of the posture feature points and calculating deviation in each posture feature point.

More specifically, referring to FIG. 9, an average position of feature points of the stand posture model may be obtained using position information of posture feature points that are manually assigned from N posture images. Assuming that a vector indicating p-th posture feature points selected from posture image collection is Zp, the Zp may be indicated in $Z_p = \{Z1_p, Z2_p, \ldots, ZN_p\}T$. At this time, the posture feature point may be expressed with an average position of posture model feature points for N posture images $\overline{Z}$ and may be calculated as following Equation 1.

$$\overline{Z} = \frac{1}{N}\sum_{p=1}^{N} Z_p \quad \text{Equation 1}$$

The deviation of the average position for the posture images, $\overline{Z}_p$, may be obtained as $d\overline{Z}_p = Z_p - \overline{Z}$.

Subsequently, the standard posture model generating module 150 analyzes change patterns for average position and deviation of the posture feature points in block S208 and generates an average posture model changeable depending on a user's level in block S210. For example, when the deviation between a horse-riding posture model of the user and the standard posture model exceeds a predetermined threshold value, it may be possible to train a horse-riding posture by calculating a posture model having a deviation within 0 to 5% from the user posture model. This may be a value that is set in consideration of security of horse-riding training and gradual lesson.

As such, when a standard posture model is generated from the standard posture model generating module 150, the standard posture model is provided to the user posture recognizing module 100.

Next, following is operations of the user posture recognizing module 100. The user posture recognizing module 100 obtains a user posture image from a vision sensor in block S212. In this case, the posture image may be user horse-riding posture for side and rear.

Subsequently, the user posture recognizing module 100 detects a user posture by minimizing surrounding environment effects for a user posture image and correctly separating only the posture region of the user in block S214.

During this operation, in order to be less affected from surrounding illumination, a user area may be detected by applying the local adaptive binarization method. Further, the user area may be detected by extracting an edge component of an image applying the secondary differentiation and then coupling its results. The local adaptive binarization method is effective when separating object areas at the low illumination or severe change of illumination in the real environment. The edge extraction method using the secondary differentiation may be used to find out edge component from image having little brightness difference. In order to properly separate the object area in the real environment in which an illumination effect may be severe. The user posture area may be separated by joining advantages of these two methods.

Next, the user posture recognizing module 100 extracts positions of shoulder, elbow, hands and feet of a user from the posture area and detects the posture characteristics of the user in block S216, and normalizes the detected posture characteristics in order to match them with the standard posture model in block S218.

Subsequently, the user posture recognizing module 100 constructs a posture characteristic template of the user based on the extracted positions of shoulder, elbow, hands and feet of a user from the posture area in block S220, and matches the horse-riding posture of the user and the standard posture model using the standard posture model provided from the standard posture model generating module 150 in block S222.

Next, the standard posture model having the maximum similarity is detected by recognizing the horse-riding posture of the user through the match of the standard posture model in block S224. When the user posture recognizing module 100 detects the standard posture model having the maximum similarity, it suggests the standard posture model appropriate for a user's level in the detected standard posture model in block S226, thereby personalized horse-riding lesson step by step in more secure manner.

That is, the user posture recognizing module 100 may geometrically change the standard basic posture model to generate a level based standard posture model. At this time, 6-dimensional parameters may be set in order to structurally change the side posture model and changeable weights may be set to distance among feature points of the standard posture model, center point of the posture change, scaling variable for changing the entire feature point changes, upper body change scaling variable, lower body change scaling variable, change weight of the level based feature point. By differently setting the scaling variables for the posture feature points based on the upper body and lower body of the standard posture model, a large posture change weight may be set to the feature points in which posture change is made with ease.

Figure 10A:
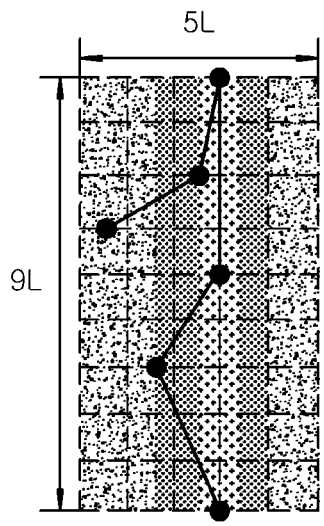
FIGS. 10A and 10B are illustrative views showing a level based posture area in a horse-riding simulator in accordance with an embodiment of the present invention.
Figure 10B:
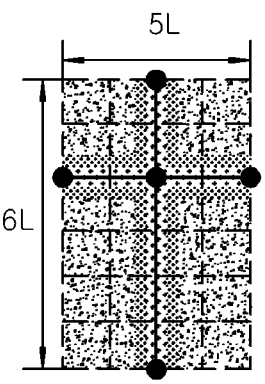
Figure 10B:
Figure 10B:
Figure 10B:

Further, for structural change of the rear posture model, 4-dimensional parameters may be set, including distance between the feature points of the standard posture model, center point of the posture change, scaling variable for changing the entire feature points, and change weight of the level based feature point. FIGS. 10A and 10B are views illustrating a level based posture area to change a level based standard posture model.

As such, in accordance with the present invention, it may be possible to provide a lesson in consideration of an individual horse-riding level, by generating a standard posture model using collected horse-riding posture images of experts, matching posture characteristics extracted from a user's horse-riding image with the standard posture model, determining a user's horse-riding level with a user's posture recognized through the matching, and suggesting a progressive standard posture model suitable to an individually differentiated lesson.

While the description of the present invention has been made to the exemplary embodiments, various changes and modifications may be made without departing from the scope of the invention. Therefore, the scope of the present invention should be defined by the appended claims rather than by the foregoing embodiments.

What is claimed is:

1. An apparatus for recognizing a user's posture in a horse-riding simulator, the apparatus comprising:
 a standard posture model generation module configured to find out a standard posture model by selecting horse-riding posture feature points from an expert database, and generate the standard posture model; and
 a posture recognizing module configured to obtain a user's posture from the horse-riding simulator, recognize a user's horse-riding posture by matching the obtained user's posture with the standard posture model generated in the standard posture model generation module, and suggest a standard posture model appropriate for a user's level.

2. The apparatus of claim 1, wherein the standard posture model generation module comprises:
 a posture image input unit configured to input horse-riding posture images of an expert;
 a feature point selecting unit configured to extract positions of a body from the horse-riding posture images of an expert inputted from the posture image input unit and select horse-riding posture feature points in the posture image;
 a posture image normalizing unit configured to normalize the horse-riding posture images of an expert inputted from the posture image collecting input unit;
 an average position and deviation extracting unit configured to calculate an average position of the horse-riding posture feature points inputted from the feature point selection unit and extract a deviation of the posture image from the average position;
 a posture deviation pattern analyzing unit configured to analyze a posture deviation and change pattern from various posture images produced depending on a user's level or walking pattern of a horse; and
 a posture model generation unit configured to generate the standard posture model by applying the posture deviation and change pattern analyzed in the posture deviation pattern analyzing unit.

3. The apparatus of claim 2, wherein the posture image collection inputting unit is configured to input the posture images of an expert from the expert database that stores the horse-riding posture images of an expert.

4. The apparatus of claim 2, wherein the feature point selecting unit extracts positions of shoulder, elbow, hands or feet from the horse-riding images and selects characteristics of the posture image.

5. The apparatus of claim 1, wherein the posture recognizing module comprises:
 an image acquisition unit configured to acquire a user's posture image;
 a posture detecting unit configured to separate the posture area from the user's posture image obtained from the image acquisition unit and detect the user's posture;
 a user's posture characteristic extracting unit configured to extract a body position of a user from the posture area and detect a posture characteristic of the user;
 a characteristic normalizing unit configured to normalize the posture characteristic of the user detected from the user's posture characteristic detecting unit; and
 a recognizing unit configured to recognize the user's horse-riding posture by matching the user's posture with the standard posture model.

6. The apparatus of claim 5, wherein the posture detecting unit is configured to detect the user's posture by minimizing a surrounding environment effect for the user's posture image obtained from the image acquisition unit and correctly separating only the posture area of the user.

7. The apparatus of claim 5, wherein the user's posture characteristic extracting unit is configured to detect the posture characteristic of the user by extracting positions of shoulder, elbow, hands or feet from the posture area of the user.

8. The apparatus of claim 5, wherein the recognizing unit is further configured to suggest a standard posture model appropriate for a user's level.

9. The apparatus of claim 5, wherein the image acquisition unit is configured to obtain the user's posture image through a vision sensor.

10. A method for recognizing a user's posture in a horse-riding simulator, the method comprising:
 finding out a standard posture model by selecting horse-riding posture feature points from an expert database to generate the standard posture model; and obtaining a user's posture from the horse-riding simulator to recognize a user's horse-riding posture by matching the obtained user's posture with the standard posture model.

11. The method of claim 10, wherein said generating the standard posture model comprises:
inputting horse-riding posture images of an expert;
extracting positions of a body from the horse-riding posture images of an expert to select horse-riding posture feature points in the posture image;
normalizing the horse-riding posture images of an expert;
calculating an average position of the horse-riding posture feature points and extracting a deviation of the posture image from the average position;
analyzing a posture deviation and change pattern from various posture images produced depending on a user's level or walking pattern of a horse; and
generating a standard posture model by applying the analyzed posture deviation and change pattern.

12. The method of claim 11, wherein the horse-riding posture image is inputted from an expert database that stores the horse-riding posture images of an expert.

13. The method of claim 11, wherein the horse-riding posture feature points are selected by extracting positions of shoulder, elbow, hands or feet from the horse-riding image.

14. The method of claim 10, wherein said recognizing the user's horse-riding posture comprises:
acquiring a user's posture image;
separating a user's posture area from the user's posture image obtained and detecting the user's posture;
detecting a posture characteristic of the user by extracting a body position of the user from the posture area of the user;
normalizing the detected posture characteristic of the user; and
recognizing the user's horse-riding posture by matching the user's posture with the standard posture model.

15. The method of claim 14, wherein said detecting the posture characteristic of the user comprises extracting positions of shoulder, elbow, hands or feet from the user's posture area to detect the posture characteristic.

16. The method of claim 14, further comprising:
suggesting a standard posture model appropriate for a user's level.

* * * * *